United States Patent [19]

Lares et al.

[11] 4,193,327

[45] Mar. 18, 1980

[54] WRENCH FOR A DENTAL HANDPIECE

[75] Inventors: Joseph P. Lares, Redwood City; Albert J. Lares, Portola Valley, both of Calif.

[73] Assignee: Lares Mfg. Co., San Carlos, Calif.

[21] Appl. No.: 942,265

[22] Filed: Sep. 14, 1978

[51] Int. Cl.² ............................................. B25B 23/08
[52] U.S. Cl. ......................................................... 81/55
[58] Field of Search ............................... 81/55, 52.4 R

[56] References Cited

U.S. PATENT DOCUMENTS

| | | | |
|---|---|---|---|
| 3,935,761 | 2/1976 | Junkel et al. | 81/55 |
| 3,960,039 | 6/1976 | Nash et al. | 81/52.4 R |
| 4,015,489 | 4/1977 | Lieb et al. | 81/55 |
| 4,033,040 | 7/1977 | Bareth et al. | 81/52.4 R |

Primary Examiner—James L. Jones, Jr.
Attorney, Agent, or Firm—Lothrop & West

[57] ABSTRACT

The usual dental handpiece has a shank with an end housing with openings therein at opposite ends of an axis. One opening reveals a non-circular spindle. The other opening, adjacent the other end of the spindle, receives a non-circular burr threadedly engaging the spindle. The wrench has a central frame adapted to extend around the housing with one end overlying one of the openings and with a second end overlying the other of the openings. One wrench end has an open-sided, non-circular slot adapted nonrotatably to engage the non-circular burr by a motion in a direction normal to the axis. The other wrench frame end has a shaft rotatable and slidable in a coaxial journal. The shaft is nonrotatably engageable with the non-circular spindle. A knob on the shaft is used in manually rotating and axially sliding the shaft within the journal. A spring urges the shaft toward one extreme position. The frame has frame stops engageable with the handpiece shank in extreme rotated positions.

5 Claims, 7 Drawing Figures

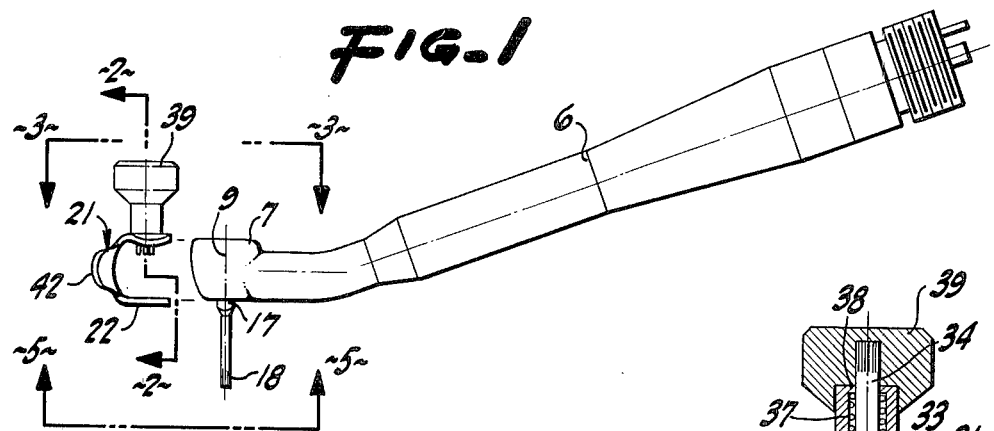
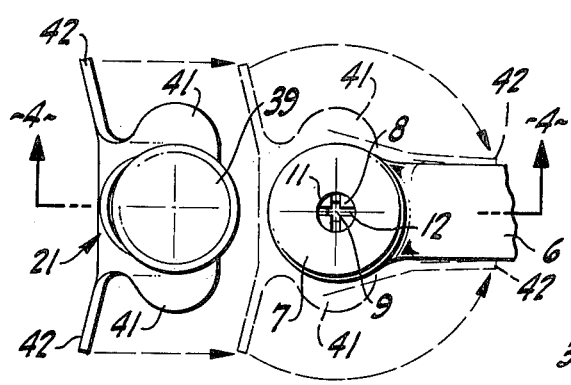
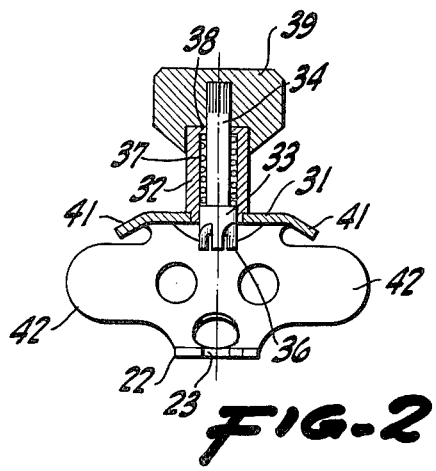
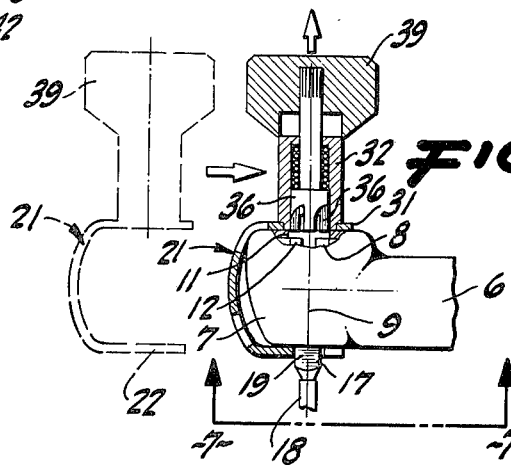
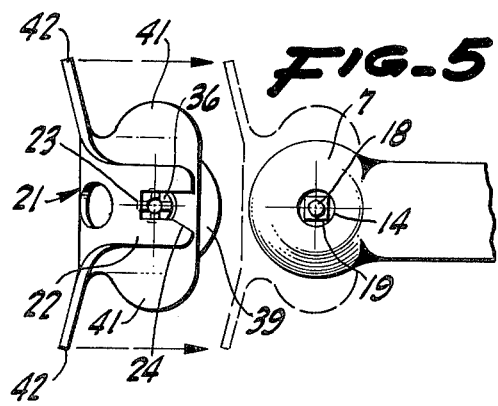
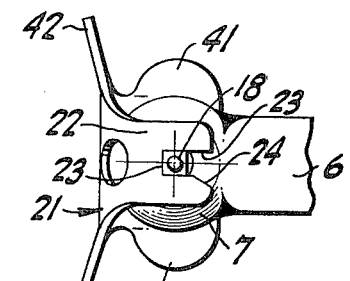
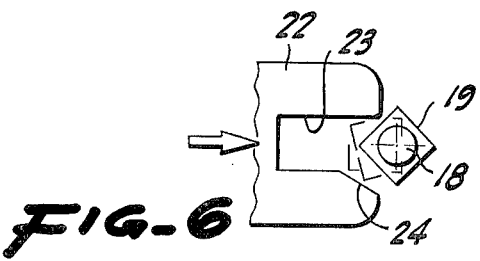

WRENCH FOR A DENTAL HANDPIECE

BRIEF SUMMARY OF THE INVENTION

Dental handpieces are generally of a similar pattern, having an elongated shank for grasping by the dentist. At one end of the shank there is a housing, sometimes circular-cylindrical and sometimes spherical. The housing has openings at opposite ends of a transverse axis, one of the openings revealing a non-circular spindle and the other of the openings revealing a threaded spindle end for receiving a threaded, non-circular burr. It is difficult to get the burr to thread and seat properly in the spindle. The shank and the spindle must be held while the burr is relatively rotated. The present wrench is adapted to be applied, utilizing one hand holding the wrench and the other hand holding the handpiece. Part of the wrench engages a non-circular part of the burr and another part of the wrench is brought to engage a non-circular part of the spindle. A knob on the wrench shaft when rotated rotates the wrench frame until the frame abuts the handpiece shank. Thereafter the wrench knob is effective relatively to rotate the burr and the spindle. The rotation can be in a direction to disengage the burr from the spindle or, in the opposite direction, to engage the burr with the spindle. When either operation has been completed the wrench is readily stripped from the handpiece for subsequent use.

BRIEF DESCRIPTION OF THE SEVERAL VIEWS OF THE DRAWING

FIG. 1 is a side elevation of a handpiece of typical construction with the wrench of the invention nearly in position for use thereon.

FIG. 2 is an enlarged cross-sectional view through the wrench, the planes of section being shown by the lines 2—2 of FIG. 1.

FIG. 3 is an enlarged top plan of the end of the handpiece and of the wrench in position for engagement therewith.

FIG. 4 is a cross-sectional view, the plane of which is shown by the line 4—4 of FIG. 3 and with the wrench in position of use.

FIG. 5 is a bottom plan view like FIG. 3.

FIG. 6 is a fragmentary bottom plan view showing the wrench engaging the burr.

FIG. 7 is a bottom plan view of the assembly of FIG. 4.

DETAILED DESCRIPTION

Although handpieces vary somewhat in their physical contours and sometimes in their internal construction, they customarily have an elongated shank 6 designed for grasping by the hand of the dentist. The shank merges with an end housing 7, usually of partly circular contour between parallel end faces. The housing 7 is or sometimes spherical contour, characterized by a central spindle 8 mounted in bearings (not shown) in the housing so that the spindle 8 is rotatable about an axis 9. One end of the spindle 8 appears through one opening 11 (FIG. 3) in the exterior, top portion or end face of the housing. This end of the spindle has a square or other non-circular terminus such as an incised cross 12 for the reception of a wrench to engage the spindle nonrotatably. The other end of the spindle 8 is threaded and is adjacent to and may even extend through a second opening 14 (FIG. 5) in the housing bottom portion or end face at the other end of the axis 9. This end of the threaded spindle can be screwed into or onto the threaded end 17 of any one of a number of different burrs 18. The burr has a non-circular end 19, in this instance square, so that engagement with a wrench is feasible.

So far, the structure described is generally standard or typical of most of the dental handpieces and burrs normally encountered.

The wrench pursuant to the invention includes a central frame 21, conveniently of originally flat metal and formed into an approximately C-shape. One frame end 22 is designed to extend under the housing 7 against the bottom portion or end face. This end 22 is cut out or notched to provide a non-circular slot 23. The slot is largely square to match and engage the square 19 of the burr but preferably has the entry 24 on one side only of the slot disposed at an angle or nonparallel to the other side of the slot 23. By simply moving the frame end 22 in a path normal to and toward the axis 9, the square end 19 on the burr is readily engaged by and may be partially rotated by the entry 24 (FIG. 6) until the square portion of the burr seats well in the interior portion of the slot with the two in relatively nonrotatable interengagement (FIG. 7). The frame 21 has a similar inturned end 31 designed to extend over the housing 7 against the top portion or end face, as shown in FIG. 4, and merging and fixed with a journal 32 concentric with the axis 9. Rotatably and slidably disposed in the journal is an enlarged bearing portion 33 of an operating pin 34. At the lower end the pin 34 has a non-circular terminus 36 or cross designed to interengage with the non-circular, depressed terminus 12 in the top of the spindle 8, passing through the opening 11 to do so. The pin 34 is normally urged to project the end 36 by a coil spring 37 at one end engaging against the bearing portion 33 and at the other end engaging with an inturned flange 38 near the top of the journal 32. The upper end of the pin 34 is nonrotatably and non-slidably engaged with a radially enlarged knob 39 or turnpiece having a knurled periphery. The spring 37 normally keeps the non-circular end 36 projected. When the knob 36 is lifted against the urgency of the spring 37, the pin 34 and the end 36 are also lifted and the end is substantially retracted into the inside of the journal 32 for clearance. The lifting motion is facilitated by short wings 41 curved away from the tapered lower portion of the enlarged knob 39. The user can press his thumb and finger against the top surfaces of the curved short wings and the tapered underside of the knob and so readily displace the knob upwardly by a sort of pinching motion.

In use, the wrench is positioned as shown in FIGS. 1 and 3, the knob 39 is lifted and the wrench is moved laterally until the notch is brought into engagement with the non-circular portion of the burr, as shown in FIG. 7. The lifted knob is positioned in axial alignment with the spindle 8 and then is released so the spring 37 drives the pin end 36 downwardly into engagement with the matching non-circular spindle terminus 12. The knob 39 is then rotated. The spindle 8 is thus rotated together with the held burr 18 and in the proper direction to unscrew the spindle and burr. This can be done one-handedly.

The frame 21 tends to rotate under such circumstances. Means are provided for limiting such rotation. Extending in two, nonradial directions from the central frame 21 are elongated ears 42. These are also curved to abut the shank 6, as shown by dotted lines in FIG. 3, when the device is rotated and also to be held in abutting position by the user's fingers or thumb, if desired. When the knob is rotated in one direction, there may also be a similar rotation of the central frame 21 until one of the ears 42 abuts the spindle 8. Thereafter the central frame 21 cannot further rotate in that same one direction with respect to the shank 6 and neither can the burr 18, nor can the central frame be readily dislodged. Continued rotation of the knob 39 produces an unscrewing action between the burr and the spindle. For engaging the burr and the spindle, the knob is turned in the reverse direction and the opposite ear 42 engages the shank and further rotation of the knob produces a tightly screwed engagement.

With a little practice the user can manipulate the wrench with one hand to engage the non-circular portion of the burr, to encompass the housing at the shank end and to engage the other end of the spindle. With the wrench so engaged, he can rotate the knob and produce connection or disconnection between the spindle and the burr. When the operation is finished he can withdraw the knob and detach the wrench easily from the handpiece, leaving it to one side for a subsequent operation.

We claim:

1. A wrench for a dental handpiece having a shank with an end housing having openings at opposite ends of an axis, one of said openings being in an end face substantially normal to said axis and revealing a non-circular spindle and the other of said openings being in another end face substantially normal to said axis and adjacent a non-circular burr threadedly engageable with said spindle, said wrench comprising a central frame adapted to extend around said housing and having a first end abutting one of said end faces and overlying one of said openings and having a second end abutting the other of said end faces and overlying the other of said openings; means at said first end defining an open-sided, non-circular slot adapted nonrotatably to engage said non-circular burr by a motion in a direction normal to said axis; means on said second end defining a coaxial journal; a pin rotatably and slidably disposed in said journal; means on one end of said pin non-rotatably engageable with said non-circular spindle; means on the other end of said pin for use in manually rotating and axially sliding said pin in said journal; and a spring engaging said central frame and said pin for urging said pin toward one extreme axial position in said journal.

2. A wrench as in claim 1 in which said slot is partly defined by a pair of opposite sides, one of said sides having a parallel portion and having a nonparallel entering end portion.

3. A wrench as in claim 1 in which said means for use in rotating and sliding said pin includes a knob projecting radially beyond said journal and spaced from said central frame, and means forming opposite tapered surfaces on said knob and on said central frame facing each other and spaced apart axially a predetermined distance so as to be forced apart when a user's finger is pressed therebetween.

4. A device as in claim 3 in which said opposite surfaces include a wing on said central frame extending radially from said axis and axially spaced from said tapered surface on said knob.

5. A device as in claim 1 in which said journal has an inturned flange, said pin has an enlarged bearing portion within said journal, and said spring surrounds said pin within said journal and is in abutment with said flange and with said bearing portion.

* * * * *